United States Patent

Gilmour

[11] Patent Number: 5,899,872
[45] Date of Patent: May 4, 1999

[54] FOOT AND ANKLE SUPPORT

[75] Inventor: Robert Farrer Gilmour, Auckland, New Zealand

[73] Assignee: Bodyworks Healthcare Limited, Auckland, New Zealand

[21] Appl. No.: 08/805,152

[22] Filed: Feb. 24, 1997

[51] Int. Cl.⁶ .............................. A61F 5/00; A61F 13/00
[52] U.S. Cl. .............................................. 602/65; 602/27
[58] Field of Search .................... 602/5, 23, 27, 602/60, 65, 6, 28, 29

[56] References Cited

U.S. PATENT DOCUMENTS

| | | | |
|---|---|---|---|
| 3,674,023 | 7/1972 | Mann | 602/65 |
| 4,323,058 | 4/1982 | Detty | 602/27 |
| 4,878,504 | 11/1989 | Nelson | 602/27 |
| 4,938,222 | 7/1990 | Bier, Jr. | 602/27 X |
| 5,000,195 | 3/1991 | Neal | 602/27 |
| 5,067,486 | 11/1991 | Hely | 602/27 |
| 5,139,479 | 8/1992 | Peters | 602/27 |
| 5,472,411 | 12/1995 | Montag et al. | 602/23 |
| 5,472,414 | 12/1995 | Detty | 602/65 X |
| 5,501,659 | 3/1996 | Morris et al. | 602/27 |

Primary Examiner—Richard J. Apley
Assistant Examiner—Denise Pothier
Attorney, Agent, or Firm—Young & Thompson

[57] ABSTRACT

A foot and ankle support including a boot element of which first and second parts are shaped and positioned to embrace respectively parts of a user's leg above, and foot in front of, the ankle. Two straps are fastened by a first fastening to the first part at a position above and not behind the position in the boot element at which the ankle will be located. The straps are adapted to cross in front of the ankle and encircle the foot. The support may also include a stiff shell including first and second upright members joined by an integral third member. The first and second members are shaped and dimensioned to fit over malleoli of a foot and to extend part way up opposite sides of a leg.

12 Claims, 2 Drawing Sheets

FOOT AND ANKLE SUPPORT

BACKGROUND

This invention relates to foot and ankle supports for human use.

Known supports of this general type are typically used to reduce the likelihood of injury to the foot and/or ankle or subtalar joint in conditions of high physical stress thereto. In addition or alternatively such supports are used to limit the local deformation of a foot or ankle which has already been injured, as a means of assisting healing processes.

It has been found that many of the known supports fail to achieve satisfactory results or impose unwanted constraints on desired movements of the foot or ankle. For example, if support straps are fastened to the support behind the ankle/subtalar joint axis, plantar flexion of the foot causes the straps to lose tension and therefore control of the foot and/or ankle or subtalar joints is reduced.

OBJECT

It is an object of the present invention to at least reduce such disadvantages.

STATEMENTS OF THE INVENTION

According to one aspect of the present invention there is provided a foot and ankle support including a boot element of which first and second parts are shaped and positioned to embrace respectively parts of a user's leg above, and foot in front of, the ankle and at least one strap fastened by a first fastening to said first part at a position above and not behind the position in said boot element at which the ankle will be located, in use, the strap or straps together being adapted to cross in front of the ankle and encircle the foot.

Preferably the or each strap is fastened to said first part in such a way that the strap extends forwardly and downwardly from said first fastening.

Conveniently the boot element includes an adjustable front fastening which enables the circumference of the boot element to be adjusted.

The adjustable front fastening may be a lace and eyelets or areas of hook-and-loop fastening material.

Preferably the or each strap is long enough to pass from said first fastening forwardly and diagonally downwardly across the top of the foot down and under the metatarsal region of the foot and diagonally backwards and upwards to a fastening for the free-end of the strap.

Conveniently the fastening for the free end of the strap is located in a region extending between levels above and below said first fastening and rearwardly of said first fastening.

The fastening for the free end may be areas of hook and loop material and said region may comprise one of the areas of hook-and-loop material.

Preferably the support includes a tightenable band positioned to encircle said first part of the boot element and to cover and hold the free ends of the straps.

Conveniently the band is elastically extensible up to a predetermined tension, after which it is substantially inextensible.

According to another aspect of the present invention there is provided a foot and ankle support including a stiff shell including first and second upright members joined by an integral third member, the first and second members being shaped and dimensioned to fit over malleoli of a foot and to extend part way up opposite sides of a leg.

Preferably the third member is at the rear of the shell.

Conveniently the third member is at the top of the first and second members and there is a gap between the first and second members in the region of the Achilles tendon.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

Various embodiments of the invention are described, by way of example only, with reference to the accompanying drawings, in which.

DESCRIPTION

Figure 1:
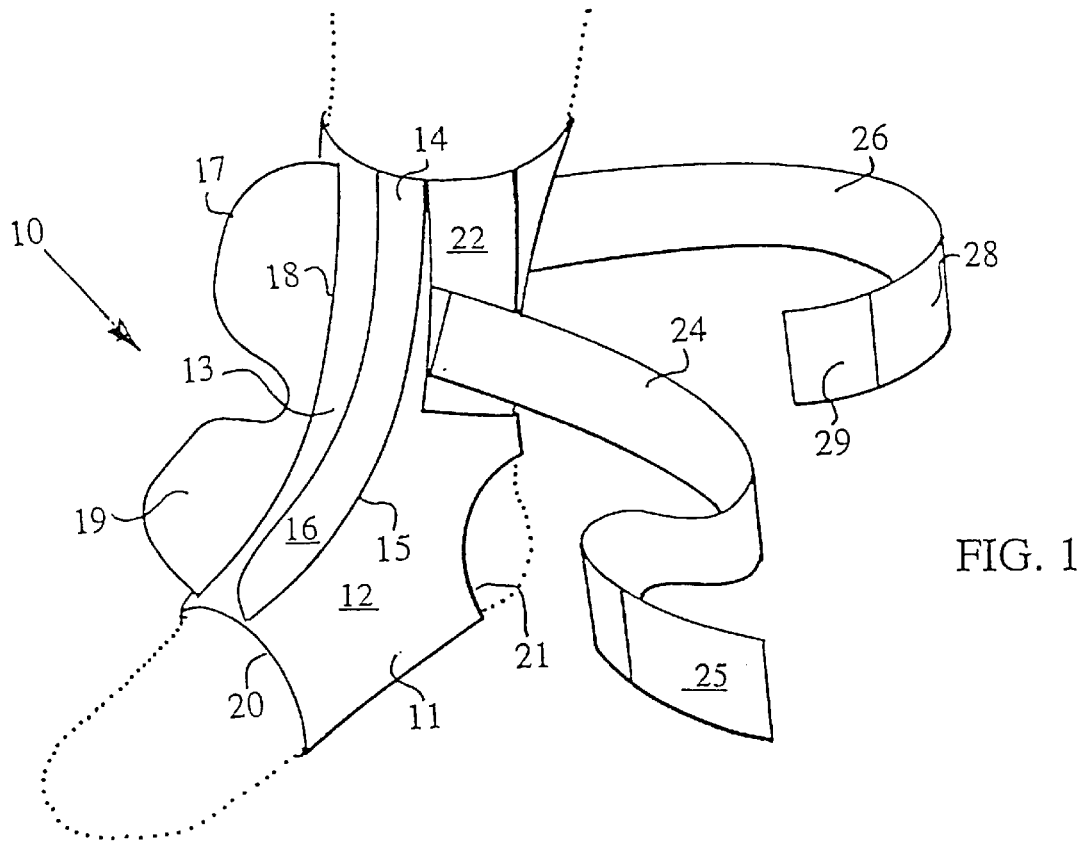
FIG. 1 is a perspective view of a foot and ankle support according to the invention.
Figure 2:
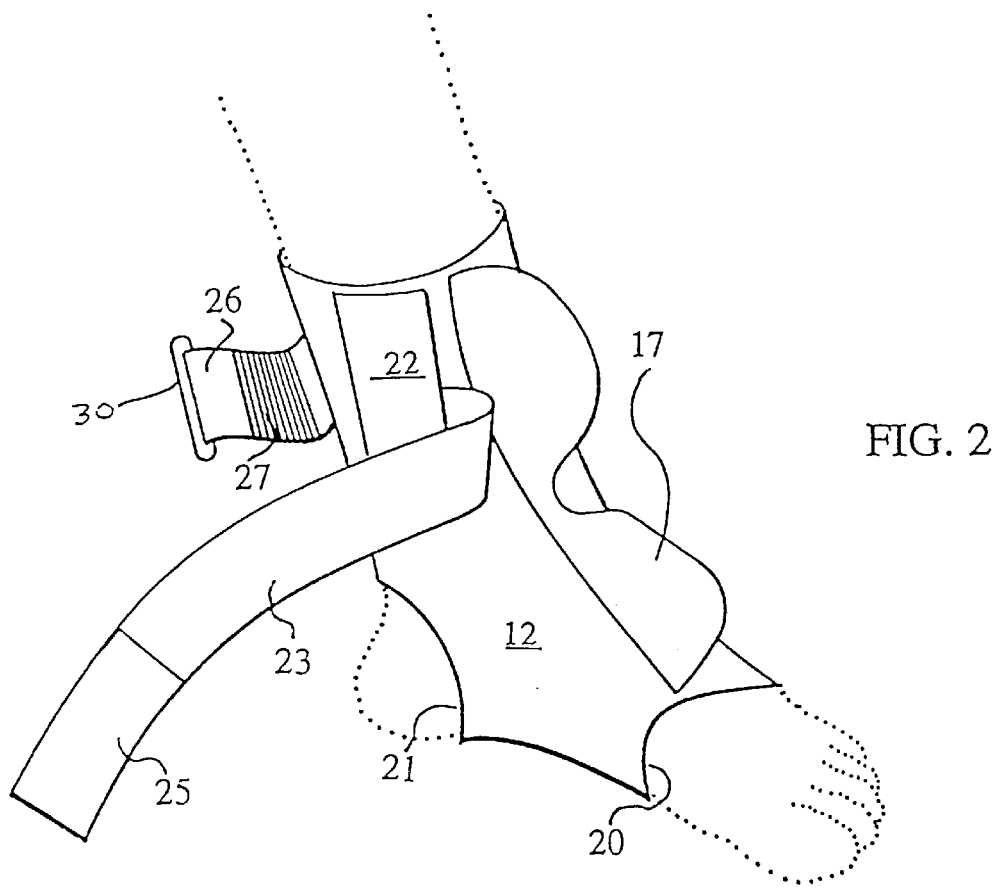
FIG. 2 is a different perspective view of the support shown in FIG. 1.

In FIGS. 1 and 2, a foot and ankle support 10 includes a boot 11 of soft material such as neoprene-based material or the like. The boot 11 is shown unfastened and has a main body 12 with a fastened-in front panel 13.

A first flap 14 is fastened along an edge 15 of the flap 14 to the body 12. The outer face 16 of the flap 14 is covered with hook-and-loop type fastener material. A second flap 17 is fastened along an edge 18 of the flap 17 to the body 12. The inner face 19 of the flap 17 is covered with hook-and-loop type fastener material, complementary to that on the face 16 of the flap 14. Alternatively other adjustable fasteners such as hooks and eyes could be used.

When the flaps 14, 17 are undone, a user's foot is inserted down and through the support 10 until the fore-foot and heel protrude through apertures 20, 21 respectively. The flap 14 is then folded flat onto the panel 13 and the flap 17 is pulled to tension the somewhat elastic material of the boot 11. The flap 17 is then laid over and onto the flap 14, thereby retaining the tension in the boot material and fastening the boot 11 firmly on the foot. The fastening such as hook and loop type fastening material allows a secure attachment between flaps 14 and 17 whilst allowing a wide range of adjustment.

Down each side of the body 12 from the top edge thereof to the region of the ankle of a user, there is affixed a panel of hook-and-loop type fastening material 22, Two fastenings straps 23, 24 are connected or fastened to the body 12 at the front edges of the panel 22. Thus, the fastened ends of the straps 23, 24 are positioned forward of and at substantially the same height as the malleoli. The straps 23, 24 are fastened so that they are oriented at an angle to the vertical. The fastening of the straps 23, 24 to the body 12 at the respective front edges of the panels 22 constitutes second fasteners.

Figure 3:
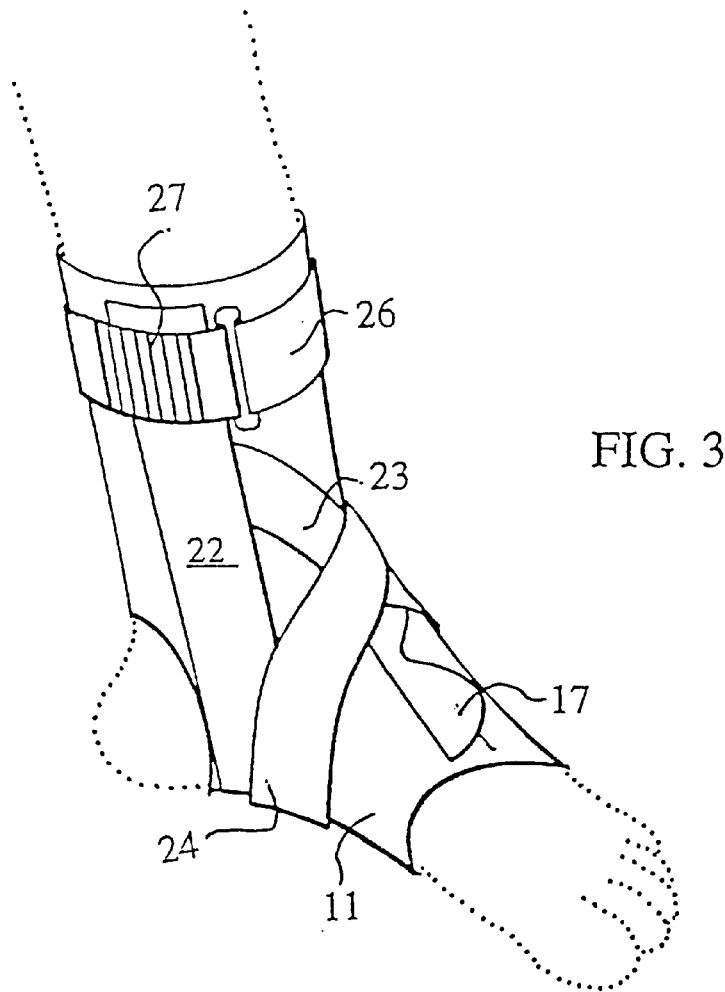
FIG. 3 is a perspective view of FIG. 2 when fastened.

In use, each band is wrapped diagonally downwards and forwards, as shown in FIG. 3, across the top of the foot, down under the metatarsal region of the foot and upwards over the adjacent one of the malleoli. The free end of each strap 23, 24 has affixed thereto a patch 25 of hook-and-loop fastening material complementary to the panels 22. Thus each patch 25 can be attached to the panel 22 on the same side of the boot 11 from which the strap 23, 24 started. The angled and forward origin of the straps 23, 24 directs them to lie naturally in the desired position under the foot, and to maintain position during plantar flexion. The correct angle for the straps depends therefore on the relative dimensions of the device but can be readily empirically determined. The fastening of the patches 25 to their respective panels 22 constitutes first fasteners.

A tightenable band 26 is fastened a short distance from one end thereof to the center rear at or near the top of the boot 11. The band 26 is generally inelastic, but includes an insert 27 of elastic material, of a type in which the tensile stiffness increases sharply at a substantially predetermined tensile load. Such elastic material is readily available and the predetermined tensile load needs be sufficient to allow the band to be adequately tensed for the purpose. Again the best material from those available is readily empirically determined. Most of the external surface 28 of the band 26 is coated with hook-and-loop type fastener material. However, a length 29 of the external surface 28 at one end is coated with a type of hook-and-loop fastening material complementary to the rest of the external surface 28. Thus, the band 26 can be wrapped around the upper part of the boot 11 and passed through a loop 30 on the band end. The band can then be pulled and tensioned up to the predetermined tensile load and fastened by applying the length 29 into the external surface 28 after passage through the loop 30.

The position of the band 26 on the boot 11 is such that, in relationship to the length of the straps 23, 24 the band 26 when fastened will lie over and retain the free ends of the straps 23, 24.

The residual elasticity in the band 26 after it has been tightened allows the natural excursion of the Achilles tendon during movement, whilst exerting maximum pressure on the ends of the straps 23, 24 .

FIG. 3 shows the relative positions of the boot 11, the flap 17, the straps 23, 24 and the band 26 after they are all fastened.

Figure 4:
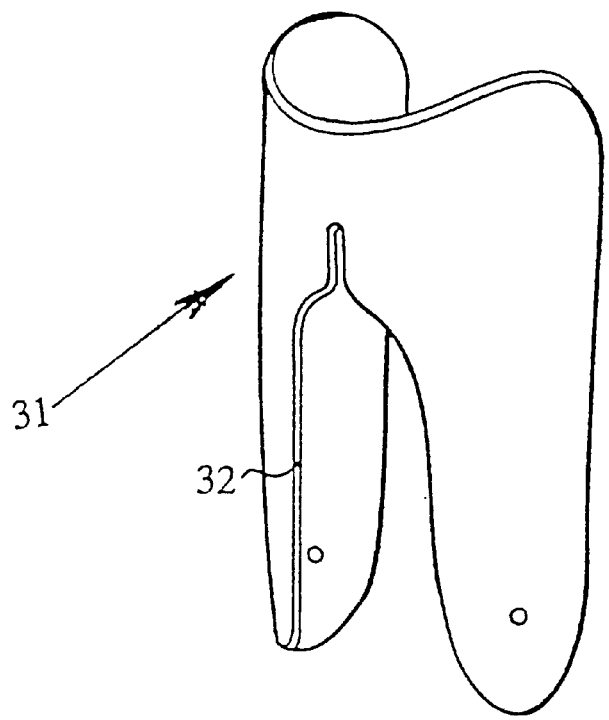
FIG. 4 is a rear perspective view of another foot and ankle support according to the invention.

FIG. 4 shows a form of loose stiff brace member 31 which has a generally U-section when viewed from above. The brace member 31 is dimensioned and shaped to be applied from the rear to the lower leg and foot and to be a snug fit thereover and over the malleoli. An opening 32 extends upwards from the bottom edge, through which opening the Achilles tendon can protrude.

In use, the brace member 31 can be fitted over the boot 11 and is bound into position by the band 26. This provides a scaffold for hind foot security. Alternatively, the brace member 31, can be used alone as a sub-frame to be bound by tape, for example in a figure-eight binding.

Use of the brace member 31 is particularly valuable after injury where immobilization is required. As the injury heals, the brace member 31 can be omitted.

Instead of the boot 11 being fastened by the flaps 16, 17 as described above, it can be fastened with a lace through eyelets, in a conventional manner.

What we claim is:

1. A foot and ankle support comprising:
    a boot element having an upper part configured to embrace a lower part of a user's leg and the user's ankle and a lower part configured to embrace the user's foot in front of the ankle, the upper part having sides configured to cover the user's ankle, each side having a first fastener that extends above a height where said boot element will embrace the ankle during use and a front configured to cover the region in front of the user's ankle; and
    two straps having a first end and a second free end, the first ends affixed to the front of said upper part at substantially the same height as where said boot element will embrace the ankle, each of said straps being affixed to extend forward and down and having a length to pass across the top of the foot and under the metatarsal region of the foot and diagonally back and up to a respective one of said first fasteners, each of the free second ends having a complementary fastener for removable attachment to said first fastener.

2. The foot and ankle support of claim 1, wherein each of said straps is fastened to said first part so that said straps extend forwardly and downwardly from said first fastener.

3. The foot and ankle support of claim 1, wherein said boot element includes an adjustable front fastener for adjusting a circumference of said boot element.

4. The foot and ankle support of claim 3, wherein said adjustable front fastener comprises one of lace and eyelet connectors, and areas of hook-and-loop fastener material.

5. The foot and ankle support of claim 1, wherein said boot element further comprises two second fasteners and said two straps are affixed to said upper part at said second fasteners.

6. The foot and ankle support of claim 1, further comprising a tightenable band positioned to encircle said first part of said boot element and to cover and hold free ends of said straps.

7. The foot and ankle support of claim 6, wherein said band is elastically extensible up to a predetermined tension, after which it is substantially inextensible.

8. A foot and ankle support comprising:
    a boot element with a first part shaped and positioned to embrace a user's leg at least at and above the ankle and a second part shaped and positioned to embrace the user's foot in front of the ankle;
    two straps, each fastened by a first fastener to said first part at a position at substantially the same height as and not behind a position in said boot element at which the ankle will be located, each strap being adapted to cross in front of the ankle and encircle the foot;
    wherein said boot element further comprises two second fasteners and wherein each of said straps has a length so that it passes from said first fastener forwardly and diagonally downwardly across the top of the foot down and under the metatarsal region of the foot and diagonally backwards and upwards to one of said second fasteners; and
    wherein said second fasteners are located in a region extending between levels above and below said first fastener and rearwardly of said first fastener.

9. The foot and ankle support of claim 8, wherein free ends of said straps comprise areas of hook-and-loop material and said region comprises hook-and-loop material.

10. A foot and ankle support comprising:
    a boot element with a first part shaped and positioned to embrace a user's leg at least at and above the ankle and a second part shaped and positioned to embrace the user's foot in front of the ankle;
    two straps, each fastened by a first fastener to said first part at a position at substantially the same height as and not behind a position in said boot element at which the ankle will be located, each strap being adapted to cross in front of the ankle and encircle the foot; and a stiff shell having first and second upright members joined by an integral third member, said first and second members being shaped and dimensioned to fit over said first part of said boot element and being held in place by said straps to extend part way up opposite sides of a leg.

11. The foot and ankle support of claim 10, wherein said third member is at a rear of said shell.

12. The foot and ankle support of claim 10, wherein said third member is at the top of said first and second members and there is a gap between said first and second members in the region of the Achilles tendon.

* * * * *

UNITED STATES PATENT AND TRADEMARK OFFICE
CERTIFICATE OF CORRECTION

PATENT NO. : 5,899,872
DATED : May 4, 1999
INVENTOR(S) : Robert Farrer GILMOUR

It is certified that error appears in the above-indentified patent and that said Letters Patent is hereby corrected as shown below:

On the title page, insert Item [30] as follows:

--[30] Foreign Application Priority Data

February 22, 1996 [NZ] New Zealand . . .286052--.

Signed and Sealed this

Twenty-sixth Day of October, 1999

Attest:

Q. TODD DICKINSON

*Attesting Officer*      *Acting Commissioner of Patents and Trademarks*